(12) United States Patent
Knaus

(10) Patent No.: US 10,869,834 B2
(45) Date of Patent: Dec. 22, 2020

(54) TREATMENT OF INFLAMMATORY BOWEL DISEASE

(71) Applicant: University College Dublin, National University of Ireland, Dublin, Dublin (IE)

(72) Inventor: Ulla Knaus, Dublin (IE)

(73) Assignee: University College Dublin, National University of Ireland, Dublin, Dublin (IE)

( * ) Notice: Subject to any disclaimer, the term of this patent is extended or adjusted under 35 U.S.C. 154(b) by 0 days.

(21) Appl. No.: 16/091,312

(22) PCT Filed: Apr. 6, 2017

(86) PCT No.: PCT/EP2017/058289
§ 371 (c)(1),
(2) Date: Oct. 4, 2018

(87) PCT Pub. No.: WO2017/174744
PCT Pub. Date: Oct. 12, 2017

(65) Prior Publication Data
US 2019/0151238 A1    May 23, 2019

(30) Foreign Application Priority Data

Apr. 7, 2016  (GB) .................................. 1605954.5

(51) Int. Cl.
| | | |
|---|---|---|
| *A61K 9/00* | (2006.01) | |
| *A61K 33/40* | (2006.01) | |
| *A61P 1/00* | (2006.01) | |
| *A61K 9/50* | (2006.01) | |
| *A61K 35/74* | (2015.01) | |
| *A61K 38/44* | (2006.01) | |
| *A61K 9/48* | (2006.01) | |

(52) U.S. Cl.
CPC .......... *A61K 9/0053* (2013.01); *A61K 9/5005* (2013.01); *A61K 33/40* (2013.01); *A61K 35/74* (2013.01); *A61K 38/443* (2013.01); *A61P 1/00* (2018.01); *A61K 9/4858* (2013.01)

(58) Field of Classification Search
None
See application file for complete search history.

(56) References Cited

U.S. PATENT DOCUMENTS

2010/0179646 A1    7/2010  Gross et al.
2014/0227367 A1*   8/2014  Huang ................. A61K 31/192
                                              424/616

FOREIGN PATENT DOCUMENTS

WO    WO-2015/192136 A1    12/2015
WO    WO-2015192136 A1 *   12/2015 ........... A61K 31/335

OTHER PUBLICATIONS

Stanley J. Swierzewski, III, M.D.Prevent Symptoms of Ulcerative Colitis (UC) (Year: 2008).*
Asanza et al: "Gastrointestinal tract injury caused by hydrogen peroxide. Report of four cases" Revista Espanola De Enfermedades Digestivas, vol. 87, No. 6, 1995, pp. 465-468.
Strus et al: "A Role of Hydrogen Peroxide Producing Commensal Bacteria Present in Colon of Adolescents With Inflammatory Bowel Disease in Perpetuation of the Inflammatory Process", Journal of Physiology and Pharmacology, vol. 60, No. Suppl. 6, Dec. 2009, pp. 49-54.
Sumimoto et al: "The Nox family of NADPH oxidases that deliberately produce reactive oxygen species", Frontiers of Gastrointestinal Research—Free Radical Biology in Digestive Diseases, 2011, vol. 29, pp. 23-34.

* cited by examiner

*Primary Examiner* — Celeste A Roney
(74) *Attorney, Agent, or Firm* — Cesari & McKenna, LLP

(57) ABSTRACT

A delivery system comprising hydrogen peroxide or a hydrogen peroxide generator system, for use in a method for the treatment or prevention of inflammatory bowel disease in a mammal, is described. The method comprises a step of orally administering to the mammal the delivery system, wherein the delivery system is formulated for oral delivery and release of the hydrogen peroxide or hydrogen peroxide generator system in-situ at a target location in the mammalian gastrointestinal tract. Also described is an oral dosage delivery system comprising hydrogen peroxide or a hydrogen peroxide generator system, in which the delivery system is configured for oral administration to a mammal and release of the hydrogen peroxide or hydrogen peroxide generator system at a target location within the mammalian gastrointestinal tract thereby effecting a localised increase in hydrogen peroxide levels at the target location in the mammalian gut or airways.

15 Claims, 8 Drawing Sheets

United States Patent 10,869,834 B2

TREATMENT OF INFLAMMATORY BOWEL DISEASE

CROSS REFERENCE TO RELATED APPLICATIONS

This application is the National Stage of International Application No. PCT/EP2017/058289, filed on Apr. 6, 2017, which claims the benefit of United Kingdom Patent Application No. 1605954.5, filed on Apr. 7, 2016. The contents of both applications are hereby incorporated by reference in their entirety.

TECHNICAL FIELD

The invention relates to methods for treatment of inflammatory bowel disease, especially ulcerative colitis and Crohn's disease. The invention also relates to an oral drug delivery system suitable for treating inflammatory diseases of the gastrointestinal tract.

BACKGROUND TO THE INVENTION

Dynamic interactions between barrier epithelia and microbiota shape the immune response of the host and its resilience to intestinal infections. Microbiota-induced programming of immune cell populations in the lamina propria and beyond, affects local and systemic immunity leading to immune tolerance. The intestinal epithelium in between provides not only physical separation, but participates in the immune defence by secreting mucus and releasing reactive oxygen species (ROS), antimicrobial peptides, chemokines and cytokines. The constant crosstalk between commensal bacteria and the epithelium is mutually beneficial by supporting nutritional needs and by providing secondary metabolites and ligands for pattern recognition receptors. Epithelial signals play a crucial role in determining the composition of the microbiota, which in turn alters epithelial functions and acts as first responder and defence system against intestinal pathogens. Pathogens can exploit these nutritional and chemical signals to overcome microbiota-mediated colonization resistance, thereby inducing an immediate generalized immune response. The key defence system in infections is ROS generation via NADPH oxidases (NOX, DUOX) by innate immune cells and the epithelium. This is exemplified by chronic granulomatous disease (CGD), an inherited immune disorder caused by loss-of-function variants in genes encoding for the NOX2 complex. NOX2 is required for production of bactericidal concentrations of superoxide and related compounds generated in the neutrophil phagosome after pathogen uptake. If this antimicrobial defence system fails, severe bacterial and fungal infections occur, as observed in CGD patients and Nox2 knockout mice. Diminished ROS generation by the NOX2 complex (e.g. CYBB, CYBA, NCF1, NCF2, NCF4) also constitutes a risk factor for developing Crohn's-like disease and early-onset paediatric IBD, presumably due to pathobiont development, alterations in immune sensing and intestinal homeostasis, and due to increased susceptibility to infections.

The intestinal epithelium expresses mainly the NADPH oxidases NOX1, NOX3, NOX4 and DUOX2. Although these oxidases generate ROS in much lower concentrations, their catalytic activity has been connected to maintaining epithelial signal transduction, mucus secretion, bacterial sensing and wound healing responses

STATEMENTS OF INVENTION

The Applicant has discovered that reactive oxygen species (ROS), and hydrogen peroxide in particular, act as a potent, negative regulator of the LEE pathogenicity island in attaching and effacing (A/E) human and murine enteropathogenic *E. coli* resulting in downregulation of bacterial virulence factors. Additionally, the Applicant has demonstrated that phosphotyrosine signalling in many bacteria, including gastrointestinal pathogens, is downregulated upon exposure to hydrogen peroxide. Both, the LEE pathogenicity island and phosphotyrosine signalling are required for virulence factor generation, and their downregulation has the effect of reducing bacterial virulence, thereby diminishing the pathology of inflammatory and infectious disease of epithelial tissue, especially in the mammalian gut (FIGS. 2-4 and 8). The Applicant has demonstrated that in-situ low dose administration of hydrogen peroxide accelerates recovery after insult, downregulates inflammation, and supports rapid tissue restitution, in an animal model of colitis (FIG. 15).

In a first aspect, the invention relates to hydrogen peroxide for use in a method for the treatment or prevention of infectious and inflammatory diseases of epithelial tissue in a mammal, for example the gastrointestinal tract or airways, in which the method comprises a step of administering to the mammal a delivery system comprising hydrogen peroxide or a hydrogen peroxide generator system, wherein the delivery system is optionally formulated for oral or inhalable delivery and release of the hydrogen peroxide or a hydrogen peroxide generator system in-situ at a target location in the mammal (for example in the gut/airways).

In one embodiment, the delivery system is formulated for oral delivery or inhaled delivery.

In one embodiment, the delivery system is formulated to release the active agent in the colon.

In one embodiment, the delivery system comprises a hydrogen peroxide generator system. Examples of suitable systems include enzyme(s) plus substrate combinations that are capable of producing hydrogen peroxide when they come into contact—specific examples are provided below. Other examples include active agent capable of localised stimulation of the host to produce hydrogen peroxide in-situ at the pulmonary or gastrointestinal epithelial tissue. In one embodiment, the active agent is an agonist that enhances NOX1 (superoxide) or DUOX2 (H2O2) activity. This can be achieved by formulating a delivery system that includes an agonist that enhances NOX1 (superoxide) or DUOX2 (H2O2) activity in the host intestinal epithelial layer (for example via Toll receptor stimulation or heterotrimeric G protein coupled receptors and calcium influx).

In an embodiment in which the delivery system comprises hydrogen peroxide, wherein the delivery system is optionally configured to stabilise the hydrogen peroxide prior to release. In one embodiment, the delivery system comprises a polymeric matrix (such as an alginate gel matrix) configured for slow release of the hydrogen peroxide in-situ at a target location in the gastrointestinal tract. Examples of polymeric matrix systems are known in the literature and are described below.

In one embodiment, the delivery system is an oral dosage delivery system.

In a second, related, aspect, the invention relates to a delivery system comprising a hydrogen peroxide or a hydrogen peroxide generator system, in which the delivery system is configured for oral or inhalable administration to a mammal and release of the hydrogen peroxide or hydrogen peroxide generator system at a target location within the mammalian gut or airways thereby effecting a localised increase in hydrogen peroxide levels at the target location in the mammalian gut or airways.

In an embodiment in which the delivery system comprises hydrogen peroxide, the delivery system typically comprises a polymeric matrix (such as an alginate gel matrix) configured for slow release of the hydrogen peroxide in-situ at a target location in the gastrointestinal tract.

In a further aspect, the invention relates to an oral dosage delivery system of the invention for use in treatment or prevention of an infectious or inflammatory disease or condition of the gastrointestinal tract.

In one embodiment, the delivery system comprises one or more coatings configured to degrade at the target location and release the hydrogen peroxide or hydrogen peroxide generator system at the target location.

In one embodiment, the coating is configured to degrade in response to a change in pH or in response to file acid, specific chemicals or specific proteases.

In one embodiment, the coating is configured to degrade in response to a change in pressure.

In one embodiment, the coating is configured to degrade in response to the presence of specific proteases.

In one embodiment, the coating is configured to degrade in response to bacterial digestion, in particular digestion by bacteria known to be present in certain target locations.

In one embodiment, the coating is configured to degrade in response to a predetermined residence time in the gastrointestinal tract.

In one embodiment, the coating is configured to degrade in the colon.

In one embodiment, the coating is configured to degrade in the ileum.

In one embodiment, the coating is configured to degrade in the alveoli of the lung.

Examples of suitable hydrogen peroxide generator systems include biological systems (for example hydrogen peroxide producing bacteria (especially genetically engineered or probiotic bacteria)) and chemical systems comprising enzymes capable of converting substrates into hydrogen peroxide. In the latter case, the hydrogen peroxide generator system may include a suitable substrate, or the enzyme may be chosen to utilise a substrate that is present in the patients' GI tract (for example glucose or other sugars).

In one embodiment, the hydrogen peroxide generator system comprises an enzyme and substrate configured to react to produce hydrogen peroxide, in which the enzyme and substrate are typically contained in separate compartments in the delivery system.

In one embodiment, the hydrogen peroxide generator system comprises an intermediate product generator system (for example a chemical generator system, or an enzymatic generator system comprising first enzyme and a substrate, configured to react to produce an intermediate product), and a second enzyme capable of converting the intermediate product into hydrogen peroxide, in which the components of the intermediate product generator system are typically contained in separate compartments in the delivery system. In one embodiment, the intermediate product is superoxide, and the second enzyme is capable of converting superoxide into hydrogen peroxide (i.e. superoxide dismutase). In one embodiment, the intermediate product generator system comprises an active agent that stimulates the product of the intermediate product, for example an agonist that enhances NOX1 and/or DUOX2 activity in the mammals gut. Examples of such agonists include Toll receptor agonists or heterotrimeric G protein coupled receptor agonists or calcium flux stimulators.

In one embodiment, the delivery system is configured to release the hydrogen peroxide or hydrogen peroxide generator system in the lower intestine (typically proximally of the colon). Examples of suitable delivery systems for use with this aspect of the invention are described below. Examples of hydrogen peroxide generator systems comprising suitable combinations of enzyme and substrate are described in more detail below.

In one embodiment, the hydrogen peroxide generator system comprises an enzyme configured to react with a substrate commonly found in the mammalian intestine (i.e. glucose) and produce hydrogen peroxide, in which the delivery system is typically configured to release the enzyme in the ileum. Examples of suitable enzymes are described below.

In one embodiment, the delivery system is substantially water-impermeable.

The invention also provides a bacterium genetically engineered to overproduce hydrogen peroxide. The bacterium may be engineered to overexpress an enzyme involved in hydrogen peroxide production, for example an oxidase enzyme or any other enzyme system that can generate superoxide, hydrogen peroxide or that can undergo any reaction that generates hydrogen peroxide. In one embodiment, the bacterium is engineered to incorporate the enzyme into the bacterial genome, optionally under the control of a promotor. The engineering may be stable or transient. In one embodiment, the promotor is an inducible promotor. In one embodiment, the promotor is a constitutive promotor. In one embodiment, the bacterium is a H2O2 producing bacterium. In one embodiment, the bacterium is a probiotic bacterium.

Other aspects and preferred embodiments of the invention are defined and described in the other claims set out below.

Definitions

"Infectious disease" means a disease characterised by an initial infection of the epithelial tissue, and includes disease localised to the epithelial tissue or disease that initiates due to an infection localised to the epithelial tissue and has spread to other organs, for example systemic disease such as sepsis. In the case of gastrointestinal infectious disease, examples would include infections caused by bacteria, virus, parasites and fungus. Bacterial infections can be caused by for example *Campylobacter, Escherichia coli, Salmonella, Shigella, Clostridium, Listeria* and *Staphylococcus* species of bacteria. In one embodiment, the disease is caused by infection of the middle and lower intestine.

"Inflammatory disease" as applied to the gastrointestinal tract means a disease or condition characterised by chronic inflammation of all or part of the GI tract, especially the middle or lower intestine. In one embodiment, the inflammatory disease is Inflammatory Bowel Disease (IBD) and includes ulcerative colitis and Crohn's disease. Both generally involve severe diarrhoea, pain, fatigue and weight loss. Other inflammatory diseases of the GI tract include collagenous colitis, lymphocystic colitis and Inflammatory Bowel Syndrome.

"Generated in-situ" means that the hydrogen peroxide is generated in the gut using a delivery system comprising a hydrogen peroxide generator system, in which the delivery system is configured to release the hydrogen peroxide or hydrogen peroxide generator system at a target location in the gastrointestinal tract.

"Target site" or "target location" means a predetermined location in the mammalian gastrointestinal tract. In one embodiment, the target site is distal of the stomach. In one embodiment, the target site is distal of the ileum. In one embodiment, the target site is the large intestine. In one embodiment, the target site is proximal of the colon. In one embodiment, the target site is proximal of the anus. Drug delivery system adapted to deliver payloads to these specific target sites are known from the literature and are referenced below.

"Hydrogen peroxide generator system" means a system capable of generating hydrogen peroxide in-situ at or close to a site of epithelial tissue in the body, for example in the GI tract or in the airways. The system may be a hydrogen peroxide generating bacteria or a combination of an enzyme (s) and a substrate, an enzyme, or an agonist capable of increasing hydrogen peroxide activity at the target location. In a preferred embodiment, the system is a substrate and an enzyme that catalyses the conversion of the substrate into hydrogen peroxide (optionally in the presence of water or any fluid available).

Examples of suitable system are provided in Table 1 below:

TABLE 1

Examples of Hydrogen Peroxide Generator Systems

| SYSTEM | COMPONENTS | USE |
| --- | --- | --- |
| Enzymatic A | Enzyme + Substrate (see Table 2) | Released at target location and react to produce H2O2 in-situ |
| Enzymatic B | Just enzyme | Released at target site and reacts with substrate in GI tract to produce H2O2 in-situ |
| Agonist | Agonist capable of causing in-situ increase in hydrogen peroxide activity at target location | Agonist is released at target location (i.e. colon) and interacts with epithelial cells to effect increase in local hydrogen peroxide levels |
| Wild-type bacteria | H2O2 producing bacterium | Delivered and/or released at target site and produces H2O2 in-situ |
| Transformed Bacteria A | Bacteria genetically modified to constitutively express or overexpress enzyme involved in H2O2 production | Released at target site and produces H2O2 in-situ |
| Transformed Bacteria B | Bacteria genetically modified to inducibly express or overexpress enzyme involved in H2O2 production + inducer | Released at target site along with inducer. Inducer effects overexpression of enzyme at target site |

Examples of hydrogen peroxide producing bacteria are provided in Table 2 of Schellenberg et al: http://journals.plos.org/plosone/article?id=10.1371/journal-.pone.0041217 Specific examples include *Lactobacillus reuteri, Lactobacillus rhamnosus*, and *Lactobacillus murinus, Lactobacillus johnsonii, Lactobacillus johnsonii* WT (NCC 533). In one embodiment, the bacterium is a wild-type bacterium. In one embodiment, the bacterium is a probiotic bacteria. In one embodiment, the bacterium is a genetically modified bacterium. In one embodiment, the bacterium is genetically engineered to express a protein that effects an increase in $H_2O_2$ production in the bacterium. In one embodiment, the protein is an enzyme that catalyses the formation of hydrogen peroxide (examples of suitable enzymes are provided in Table 1 below). In one embodiment, the bacterium is stably transfected in which the transgene is under the control of an inducible or constitutive promotor. In one embodiment, the bacterium is transiently transfected. Recombinant production of $H_2O_2$ by heterologous expression of an $H_2O_2$ producing entity (likely an enzyme) in bacteria is described in:

1. Patent WO 2011073956 A2-Heterologous Host
   This invention is related to bacterial engineering and the heterologous expression of useful compounds.
2. Ongley S E, Bian X, Neilan B A et al. Nat. Prod. Rep. 30:1121, 2013
3. Geldart K, Forkus B, McChesney E et al. Pharmaceuticals 9:60, 2016
4. Amiri-Jami M, Abdelhamid A G, Hazaa M et al. FEMS Microbiology Letters 362:1, 2015.

Examples of enzyme and substrate combinations that may be employed in the hydrogen peroxide generator system are described in Table 1 below.

TABLE 2

Examples of enzyme-substrate combinations

| ENZYME | SUBSTRATE |
| --- | --- |
| Glucose oxidase | Glucose |
| Xanthine oxidase | Various purines (i.e. xanthine) |
| Superoxide dismutase | Superoxide |
| Polyamine oxidase | Spermine or spermidine |
| D-amino acid oxidase | D-amino acids |
| Acyl-CoA oxidase | Fatty acids |
| Cytochrome P450 | Various |

Examples of enzymes that may be employed in the hydrogen peroxide generator system in the absence of substrate are enzymes that catalyse the conversion of substrates present in the GI tract into hydrogen peroxide. Given that the GI tract, especially the ileum, generally contains various sugars including glucose, amino acids, purines, fatty acids, most of the enzymes in Table 1 above could be employed in this context.

"Delivery system" means a drug dosage form that can be ingested or inhaled and that contains hydrogen peroxide or a hydrogen peroxide generator system and is capable of releasing the hydrogen peroxide or hydrogen peroxide generator system at a defined location in-vivo. Examples include oral dosage forms and inhalable dosage forms.

"Oral dosage delivery system" means a drug dosage form suitable for administration via the oral route that contains hydrogen peroxide or a hydrogen peroxide generator system and is designed for protecting hydrogen peroxide or the generator system during gastric transit and release of the hydrogen peroxide or generator system in the GI tract distal of the stomach, for example in the ileum or the lower intestine. In one embodiment, the delivery system is a capsule. In one embodiment, the delivery system is a solid dosage form. In one embodiment, the delivery system comprises at least two compartments configured for keeping two or more components separate prior to release (i.e. enzyme and substrate). In one embodiment, the delivery system comprises a coating that encapsulates the hydrogen generator system. In one embodiment, the coating is a pH sensitive coating. In one embodiment, the coating is a water sensitive coating. In one embodiment, the coating is a pressure sensitive coating. In one embodiment, the coating is sensitive to bile acids. In one embodiment, the generator system comprises a substrate and enzyme, in which the substrate is coated in a first coat, the enzyme is coated in a second coat, and the coated enzyme and coated substrate are optionally coated in a third coat or contained within an outer container configured to release the contents at a target location in the gastrointestinal tract (for example a gelatine capsule). In one embodiment, the delivery system comprises a matrix, especially a 3-D polymeric matrix, capable of breaking down in-situ at a target location in the gastrointestinal tract and release (typically slow release) of the hydrogen peroxide or hydrogen peroxide generator In one embodiment, the delivery system comprises a nanoparticulate or microparticulate composition. Examples of suitable drug delivery systems, including oral dosage delivery systems, capable of releasing contents at a predetermined target location in the gastrointestinal tract, and/or keeping contained components separate, and/or preventing reaction between two contained components, are known in the literature, for example:

Sathish et al (Int. J. Pharm. Sci. 2013; 258-269);
Kushal et al (Int. Res. J. Pharm. 2013, 4(3));
Philip et al (Oman Med J. 2010, 25(2));
Polymers for controlled drug delivery—Peter Tarcha (CRC Press, 21 Nov. 1990);
Pharmaceutical coating technology—Michael Aulton et al (Taylor & Francis 27 Oct. 1995);
http://www.slideshare.net/Balimusale/oral-controlled-drug-delivery-system;
European Patent No: 2418968 (Teagasc); and
European Patent No: 2097072 (RCSI).
Brayden et al. (European Journal of Pharmaceutical Sciences 79 (2015), 102-111.
Tambuwala et al. (Journal of Controlled Release 217 (2015) 221-227.
Zhang et al. *Evaluation of alginate-whey protein microcapsules for intestinal delivery of lipophilic compounds in pigs* (J. Sci. Food Agric. (2015).
Lamprecht et al. (Journal of Controlled Release 104 (2005) 337-346.
Hua et al. (Nanomedicine: Nanotechnology, Biology and Medicine 11 (2015) 1117-1132.
Drug Delivery: Fundamentals and Applications (Chapter 7, Oral Drug Delivery, Hillary and Brayden)
US2016058709 discloses an oral dosage form comprising a core of one component and an enteric coating comprising a second component
WO2016003870-bi-layer dual release probiotic tablet
WO2015132472-capsules or tablets with controlled release layers
GB2540130-oral dosage form for controlled release of enzyme and substrate
US2015343067-monolithic peroral dosage form
IN2829MU2009-oral dosage form containing two components that are kept separate and are released in the gastrointestinal tract
US2015132344-Oral leptin formulations
US2008020041-enteric coated compositions
U.S. Pat. No. 6,132,771-oral pharmaceutical dosage form As used herein, the term "agonists for NOX1" means an agent that can activate the NOX-1 gene. Agonists include Toll receptor agonists, protein kinase C or similar agonist. As used herein, the term "agonists for DUOX2" means an agonist that can induce calcium release or calcium influx (e.g. via stimulation of G protein coupled receptors), for example ATP or S1P, and agents that stimulate transcriptional upregulation of DUOX2 and/or DUOXA2 (e.g. various cytokines, bacterial ligands, mechanical, gaseous, chemical, endoplasmatic or other cell stressors).

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes), or prolongs the remission period of the disease, or prevents or delays recurrence or "flare-ups" of the disease or symptoms. In this case, the term is used synonymously with the term "therapy". In one embodiment, the delivery system is administered to the subject every day once or multiple times, or every 2, 3, 4, 5, or six days, weekly, every two weeks, or monthly. In one embodiment, the delivery system is administered to the subject during a period of remission, and optionally during a period of resurgence of the symptoms of the disease. In one embodiment, the use is to prolong a period of remission of the disease.

Additionally, the terms "treatment" or "treating" refers to an intervention (e.g. the administration of an agent to a subject) which prevents or delays the onset, remission or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure. In terms of enzyme and substrate, the hydrogen peroxide generator system may contain 0.01 mg to 100 mg of enzyme or substrate, for example 0.01 mg to 1.0 mg, or 0.1 mg to 10 mg, or 1 mg to 100 mg, depending on the identity, location or severity of the indication being treated, the size of the mammal and other variables. In one embodiment, the hydrogen peroxide generating system is configured to produce 5 nmol to 201 µmol hydrogen peroxide at a target site, typically a target site in the gastrointestinal tract, over a suitable period, for example over a period of 12 hours, 24 hours, 2, 3, 4, 5, 6, 7, 8, 9, 10, 11, 12, 13 or 14 days. The correct dosage may be determined by the attending physician.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

All publications, patents, patent applications and other references mentioned herein are hereby incorporated by reference in their entireties for all purposes as if each individual publication, patent or patent application were specifically and individually indicated to be incorporated by reference and the content thereof recited in full.

DETAILED DESCRIPTION OF THE INVENTION

Figure 1:
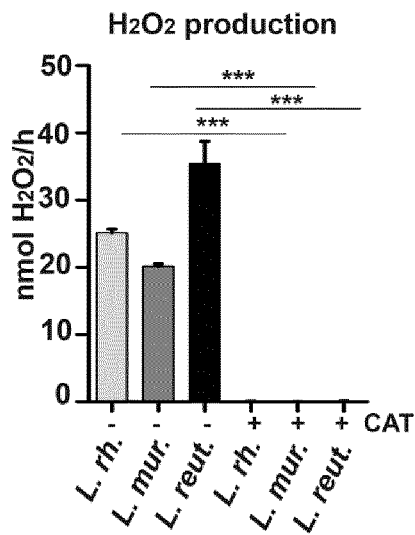
FIG. 1. Lactobacilli generate $H_2O_2$—$H_2O_2$ release by *L. rhamnosus*, *L. murinus* and *L. reuteri*. Catalase (CAT; 25 U/ml) was used for $H_2O_2$ decomposition; n=3.
Figure 2:
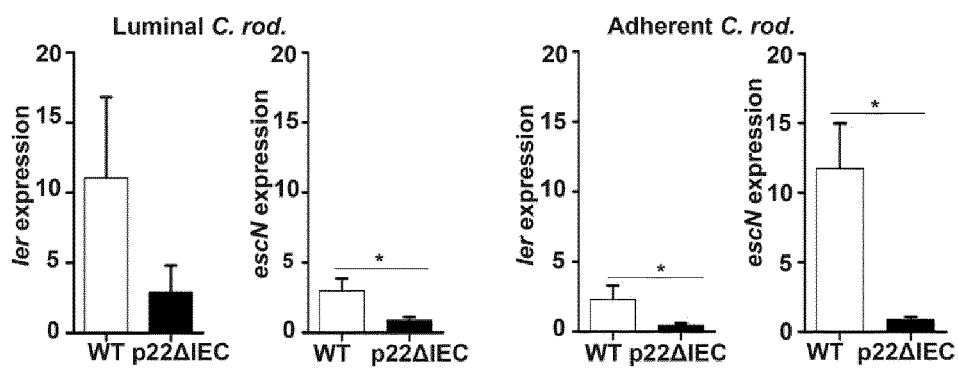
FIG. 2. Downregulation of virulence genes located in the LEE pathogenicity island (ler, escN) in *C. rodentium* infected, genetically modified mice (cyba $^{f/f}$ Vilcre) with highly increased abundance of indigenous lactobacilli (e.g. *L. reuteri*, *L. murinus*). qPCR analysis of ler and escN expression in *C. rodentium* isolated from the lumen (I) or mucus (J) of infected mice (6 dpi); n=5.
Figure 3:
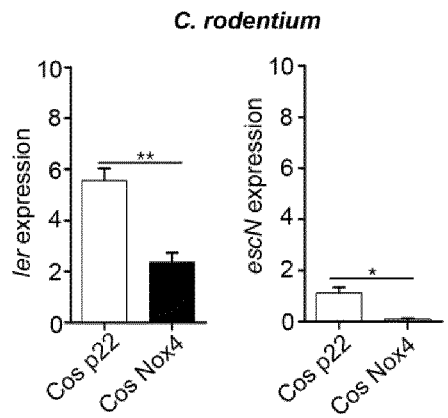
FIG. 3. Downregulation of LEE island genes after exposure of *C. rodentium* to $H_2O_2$ generated by engineered Cos cells overexpressing constitutively active NADPH oxidase NOX4. qPCR analysis of ler and escN expression in *C. rodentium* after exposure to Cos-p22 (negative control) and Cos-NOX4 cells (4 h, DMEM); n=4. Cells and bacteria were separated by a filter.
Figure 4:
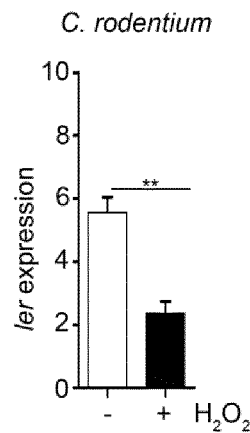
FIG. 4. Downregulation of ler in *C. rodentium* exposed to $H_2O_2$—*C. rodentium* in DMEM was treated with a single bolus of 1 mM $H_2O_2$ and analysed by qPCR for ler expression 3 h later.
Figure 5:
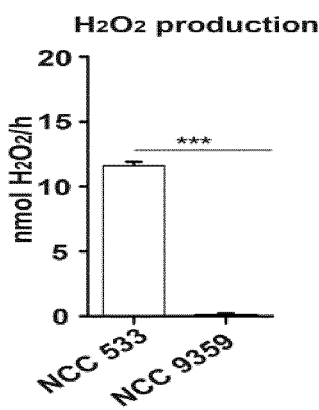
FIG. 5. $H_2O_2$ generation of *Lactobacillus johnsonii* wildtype (NCC533) and isogenic ROS source deletion mutant (NCC9359). $H_2O_2$ release by *L. johnsonii* WT NCC533 and isogenic NADH-dependent flavin reductase deletion mutant NCC9359; n=3.
Figure 6:
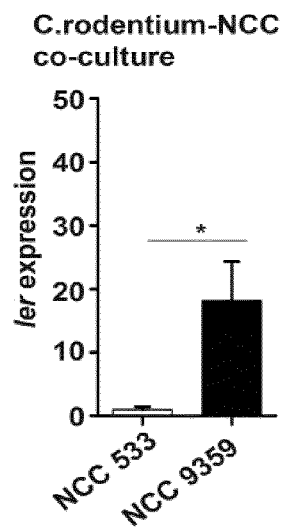
FIG. 6. $H_2O_2$-producing *L. johnsonii* NCC533, but not the mutant strain (NCC9359) downregulates the *C. rodentium* ler gene. qPCR analysis of ler expression in *C. rodentium* cultured in NCC533- or NCC9359-derived culture supernatant for 3 h; n=5.
Figure 7:
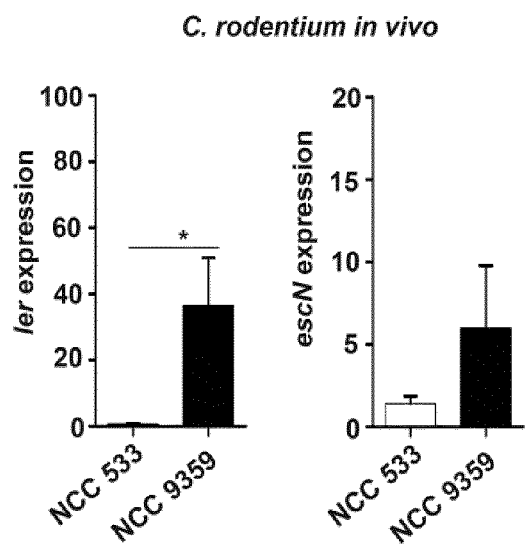
FIG. 7. Association of wildtype C57Bl/6 mice with NCC533 ($H_2O_2$ producing), but not with NCC9359 downregulates *C. rodentium* virulence genes. qPCR analysis of ler and escN expression in *C. rodentium* isolated from the lumen of infected WT3 mice at 6 dpi. Mice were pretreated and treated with NCC533 or NCC9359 during infection; n=4-5.
Figure 8:
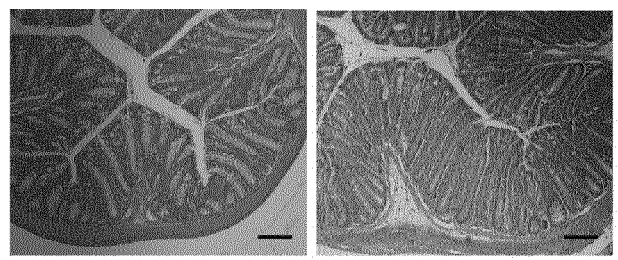
FIG. 8. $H_2O_2$ production by *L. johnsonii* is required to prevent host epithelial tissue damage during *C. rodentium* infection. C57Bl/6 mice were treated using daily oral gavage with NCC533 or NCC9359 prior and during infection with *C. rodentium*. Immunohistochemistry images (H&E staining) of representative colon sections, 6 dpi, scale bar 100 µm.
Figure 9:
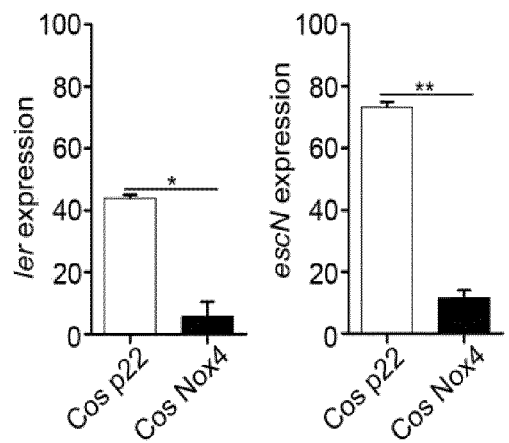
FIG. 9. Downregulation of LEE island genes in the human pathogen EPEC by exposure to $H_2O_2$ generated by Cos-NOX4 cells. Exposure of EPEC to $H_2O_2$ released from Cos-NOX4 cells (but not from Cos-p22 cells; description of cells in Cell Signal 18:69-82, 2006; J Biol Chem 283:35273-82, 2008; Mol Cell Biol 30:961-75, 2010) for 3 h followed by qPCR analysis for ler and escN expression in EPEC. Cells and bacteria were separated by a filter.
Figure 10:
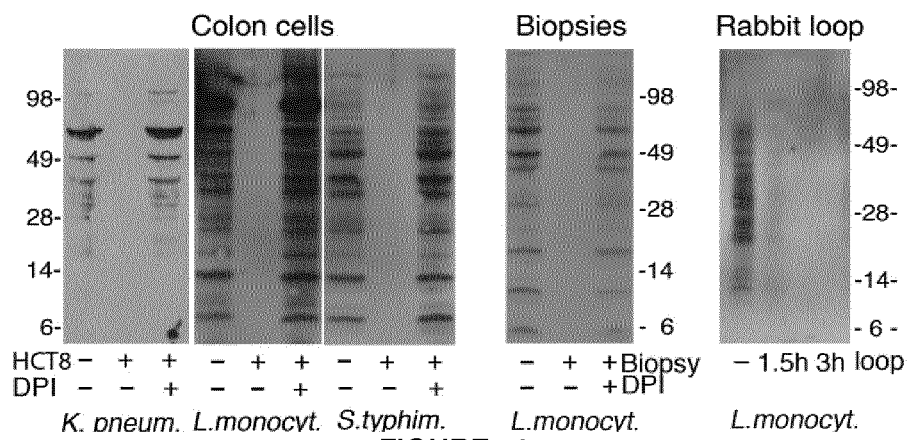
FIG. 10. $H_2O_2$ generated by colon cells, human biopsies and in the rabbit loop model during pathogen exposure downregulates bacterial phosphotyrosine signalling, which acts as virulence modifier. Anti-phosphotyrosine immunoblots of lysates derived from extracellular bacteria after co-culture (3 h) with HCT-8 colon cells (left panel) or human biopsies (middle panel), or at indicated time points after injection into rabbit ileal loops (right panel).
Figure 11:
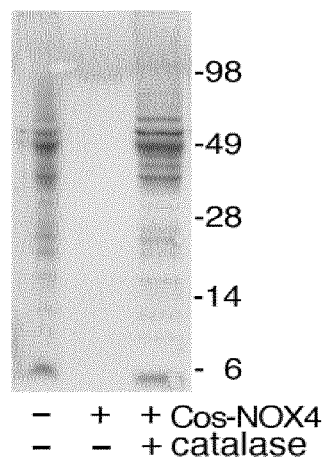
FIG. 11. Cos-NOX4 cell-produced $H_2O_2$ leads to a marked decrease in bacterial phosphotyrosine content. Anti-phosphotyrosine immunoblot of lysates derived from *L. monocytogenes* after exposure to Cos-NOX4 cells or Cos-p22 cells seeded into the lower chamber of a Boyden chamber.
Figure 12:
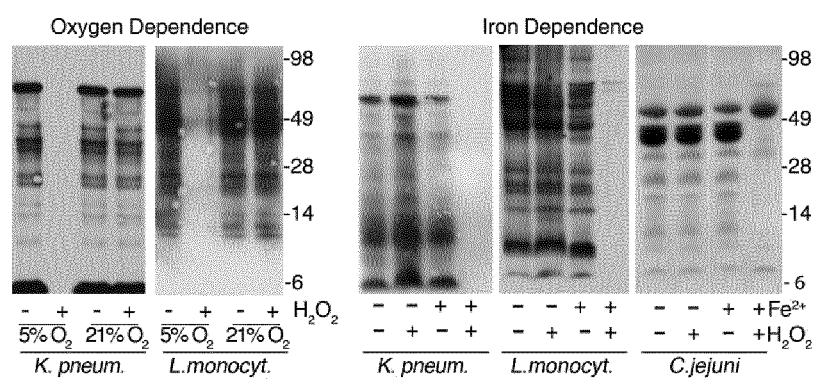
FIG. 12. Addition of $H_2O_2$ decreases bacterial phosphotyrosine content when iron is present (iron and 5% oxygen are the normal conditions in the gut). Anti-phosphotyrosine immunoblots of bacteria cultured in 5% or 21% $O_2$ (left panel) or in low or high iron conditions at 5% $O_2$ (right panel) prior to 0.7 mM $H_2O_2$ addition (3 h).
Figure 13:
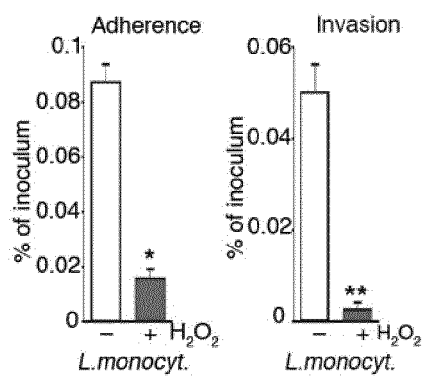
FIG. 13. *L. monocytogenes* adherence and invasion of colon cells is reduced after prior exposure of bacteria to $H_2O_2$. Bacteria were pretreated with 0.7 mM $H_2O_2$ for 3 h (bacteria remained fully viable after treatment). Adherence and invasion to HCT-8 cells was analysed as described in Cell Host Microbe 12:47-59, 2012. Error bars represent SEM and asterisks indicate significance (** $p<0.01$ and * $p<0.05$).
Figure 14:
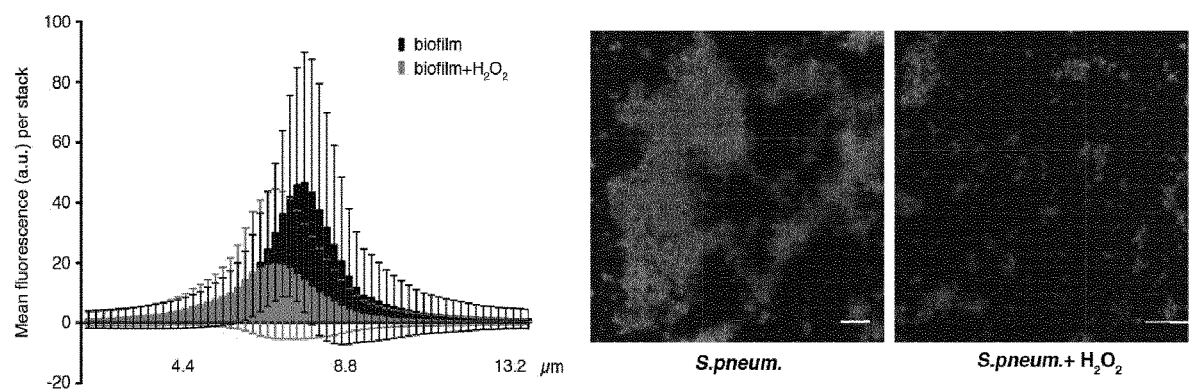
FIG. 14. Reduced biofilm formation by *S. pneumoniae* after prior exposure to $H_2O_2$. Bacteria were pretreated with 0.7 mM $H_2O_2$ for 3 h (bacteria remained fully viable after treatment) before biofilm formation was assessed. 3D measurement of *S. pneumoniae* biofilm in the presence (red) or absence (black) of $H_2O_2$ is shown (mean fluorescent values for images in a 13.5 µm thick stack). Representative confocal image of *S. pneumoniae* biofilm (green) used for quantification. Scale bar 10 m.
Figure 15:
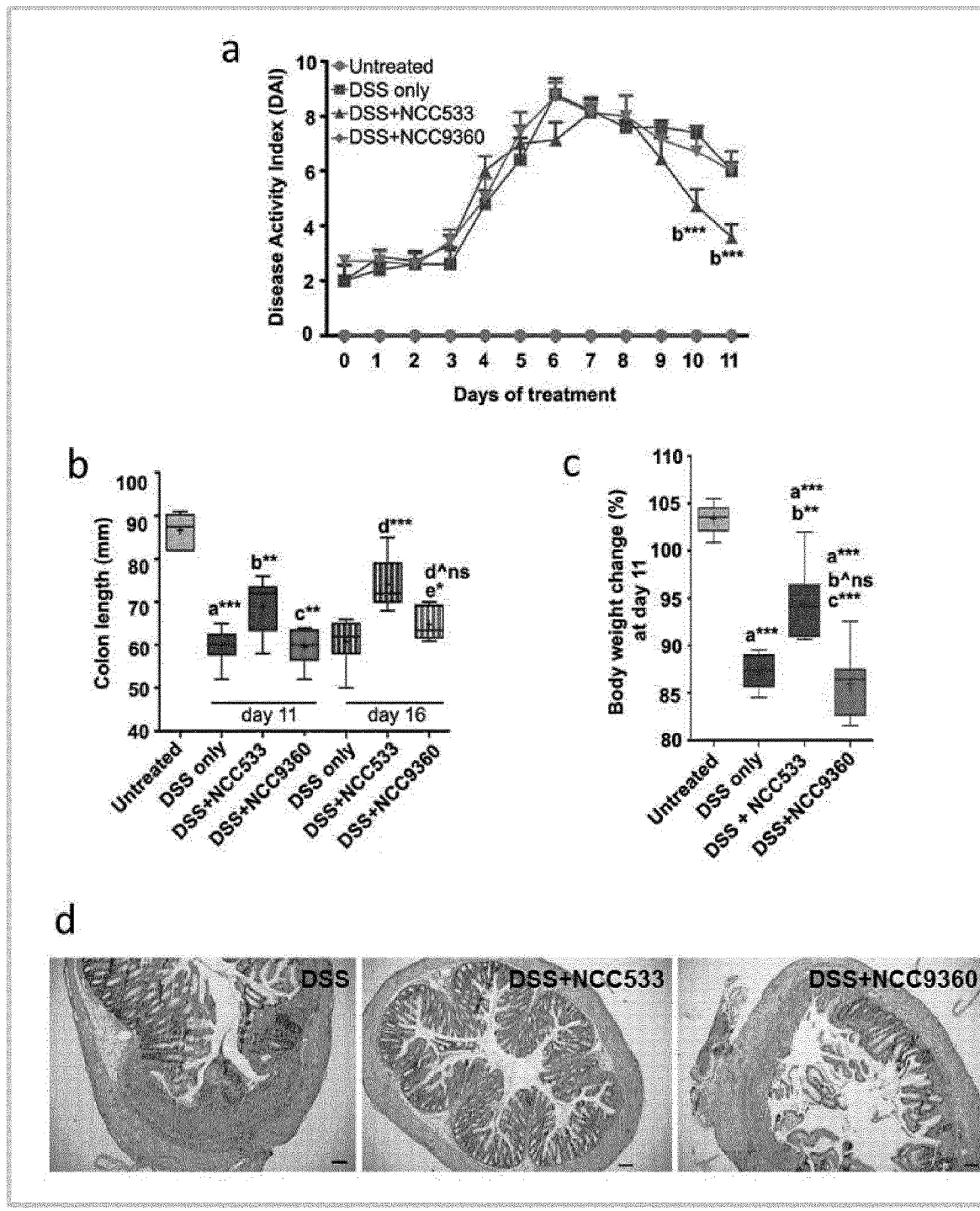
FIG. 15: $H_2O_2$ accelerates recovery in murine colitis. Mice were treated with $1\times10^9$ bacteria by daily oral gavage 5 days before, during colitis (3% DSS in water) and until the end of the experiment (day 16). On day 7 of DSS treatment, DSS was replaced with water to enable the healing process. *Lactobacillus johnsonii* wildtype (NCC533, $H_2O_2$ production) enhances tissue restitution and reduces inflammation, while an isogenic *L. johnsonii* mutant (NCC9360, Δnfr, deletion of the $H_2O_2$-generating enzyme) is not effective. Daily administration of low nanomolar $H_2O_2$ accelerates recovery after insult (a—disease index, NCC533 triangle, c—body weight), downregulates inflammation (b, colon length as indicator of inflammation), and supports rapid tissue restitution (d-H&E staining of colon day 11). One-way Anova with Tukey post-hoc test; p=0.01, *p=0.001.
Figure 16:
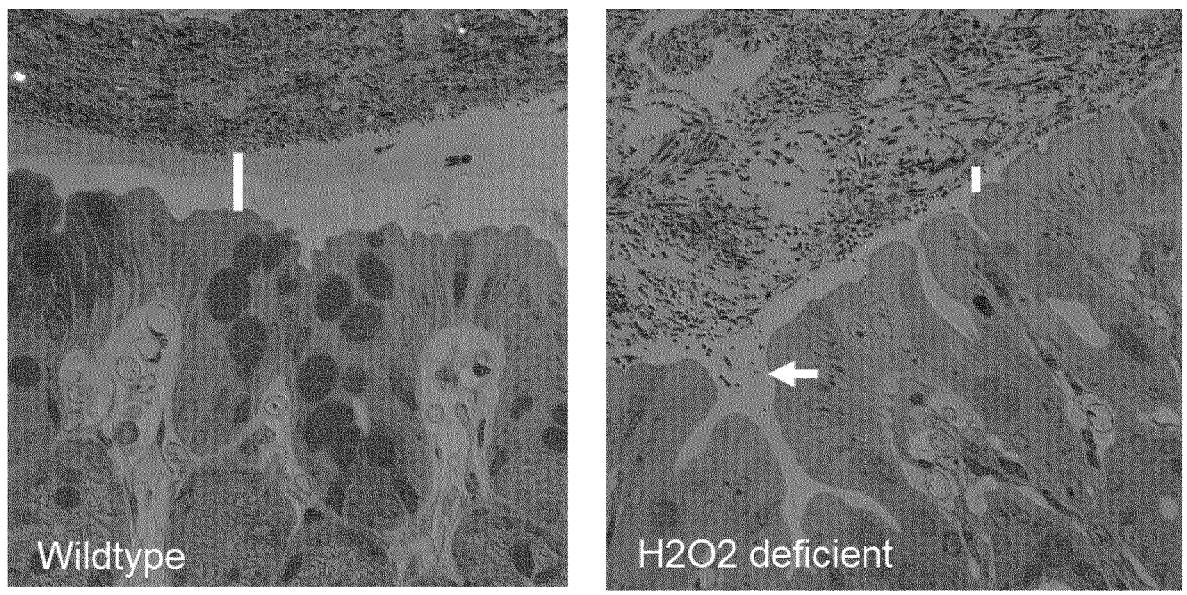
FIG. 16: Deficiency of $H_2O_2$ generating enzymes (NOX) in the colon epithelium of mice leads to reduced or even abolished mucus when compared to normal wildtype mice (white line). In wildtype mice (and humans) the mucus layer provides an impenetrable barrier and separates the intestinal bacteria (microbiota) from the host epithelium. Loss of this protective mucus layer in $H_2O_2$-deficient mice leads to bacterial colonization in crypts (arrow). Adding $H_2O_2$ can restore mucus secretion (Birchenough G. et al., Science 352:1535-1542, 2017).

Mice:

$Cyba^{flox/flox}$ mice were bred to B6.SJL-Tg (Vil-cre) 997Gum/J mice (Jackson Laboratories) to generate mice with a targeted deletion of $p22^{phox}$ in the epithelium of the small intestine and colon (p22ΔIEC). Mice were infected by oral gavage with 0.3 ml of an overnight culture of Luria Bertani broth containing $5 \times 10^9$ Citrobacter rodentium and analyzed at day 6 post infection. L. johnsonii NCC533/NCC9359 pretreatment and treatment: L. johnsonii NCC533 and NCC9359 strains were administered at a concentration of $10^9$ CFU to WT mice via oral gavage starting 3 days prior C. rodentium inoculation and daily during C. rodentium infection. For histopathology Carnoy-fixed distal colons were embedded in paraffin and 5 μm sections were stained with hematoxylin and eosin (H&E).

Cell Experiments:

Cos-NOX4 and Cos-p22 cells in DMEM, 5% FBS (Cell Signal 18:69-82, 2006; J Biol Chem 283:35273-82, 2008; Mol Cell Biol 30:961-75, 2010) were seeded into the lower chamber of a Boyden chamber (pore width 0.4 μm) 48 h before the assay. Lactobacilli grown in DMEM were suspended in media onto the upper chamber. Co-culture was initiated for 3-4 h in DMEM, 5% FBS media followed by harvesting of bacteria on the filter for RNA isolation.

Analysis of C. rodentium Virulence-Associated Genes:

Luminal content and adherent, mucus associated scrapings were obtained from infected mice (6 dpi) and used for RNA isolation. Total RNA was isolated using RNeasy Mini Kit and reverse transcribed using the High Capacity cDNA Reverse Transcription Kit. Quantitative real-time PCR for ler and escN expression was performed using a SYBR Green Master mix and normalized to the expression of gfp expressed in C. rodentium. Relative expression was determined as fold expression in comparison to LB grown C. rodentium.

In Vitro Analysis of Lactobacilli:

To obtain a cell free supernatant (CFS) the culture of lactobacilli (24 h) was centrifuged at 10000 g for 30 min (4° C.); the supernatant was collected and passed through a sterile 0.22 μm filter unit Millex GS. An exponential culture of C. rodentium ($10^4$ CFU, 500 μl) was incubated with CFS (500 μl) at 37° C. for 4 h. In other experiments lactobacilli were grown o/n in MRS to a total density of $10^9$ CFU/ml and resuspended in PBS. After 30 min incubation, the lactobacilli cultures were centrifuged at 14000 rpm (5 min) and 10 ul of the supernatant was used to measure $H_2O_2$ by Amplex Red assay.

Co-Culture of Intestinal Bacteria with Cells in Normal or Iron-Modified Conditions Bacteria in RPMI 1640 containing 3% FBS ($OD_{600}$=0.4; $10^7$ bacteria, 1 ml) were incubated with HCT-8 cells at 37° C. in microaerophilic conditions with MOI 50. DPI pretreatment of HCT-8 cells was for 20 min (25 μM). Non-adherent bacteria were removed by centrifugation of media (3300 g, 5 min), and were used for immunoblotting. Viable counts were performed for inocula to ensure that comparable numbers of live bacteria were present for each bacterial strain. Exposure of bacteria to $H_2O_2$ released by Cos cells stable expressing the NOX4-$p22^{phox}$ complex or as negative control Cos cells expressing only $p22^{phox}$ was performed using Boyden chambers. Cells in DMEM, 10% FBS medium were seeded into the bottom chamber 24 h before start of the experiment and then moved to microaerophilic conditions for 3 h. Bacteria grown in microaerophilic conditions were resuspended in 5% $O_2$ conditioned DMEM, 3-10% FBS medium, placed on top of the filter (3 μm pore size) and incubated for 3 h. Bacteria were harvested from the filter for analysis.

Quantification of Protein Phosphotyrosine Levels in Modified Iron Conditions

C. jejuni 81-176, L. monocytogenes EGDe and K. pneumoniae were grown microaerophilic to mid-log phase in minimal essential media. Bacteria were collected by centrifugation (5000 rpm, 10 min) and diluted to $OD_{600}$=0.2 in MEM. Iron (II) sulfate (40 μM) was added as indicated and cultures were grown microaerophilic until $OD_{600}$=0.5 was reached. To C. jejuni 81-176 cultures 5 mM $H_2O_2$ was added and the growth continued microaerophilic for 8 h. L. monocytogenes and K. pneumoniae cultures were exposed to 0.7 mM $H_2O_2$ for 3 h in microaerophilic conditions. Bacteria were then diluted to $OD_{600}$=0.2, collected by centrifugation, washed twice with 25 mM Tris-HCl, resuspended in 30 μl Laemmli buffer and heated for 5 min at 95° C. Boiled samples were loaded on 10% SDS-PAGE gels, separated by electrophoresis and immunoblotted. The control samples followed an identical protocol without supplemental iron or added $H_2O_2$.

Various Methods

Invasion and adhesion assays were performed as previously reported (Cell Host Microbe 12:47-59, 2012). Bacterial cell viability was assessed using the XTT (2,3-Bis-(2-Methoxy-4-Nitro-5-Sulfophenyl)-2H-Tetrazolium-5-Carboxanilide) assay. For in vitro experiments bacteria were exposed at time zero once to 0.7 mM $H_2O_2$, except for C. jejuni (5 mM), and analyzed after indicated time periods (up to 3 h, except C. jejuni up to 6 h).

Biofilm Assay

Biofilm was analyzed using SYTO9. Cultured bacteria were grown in microaerophilic conditions overnight. The bacterial culture was then adjusted to $OD_{600}$=0.1 and 1 ml of this solution was added to an optical grade plastic bottom μ-plate 24 well. Bacteria were incubated for an additional 72 h in microaerophilic conditions. Bacteria were washed gently with autoclaved water to remove planktonic cells and fixed with 3% paraformaldehyde in PBS for 1 h. Images were then analyzed for total intensity of SYTO9 fluorescence over the imaged volumes using Fiji. Briefly, after staining with SYTO9, 50 independent 13.2 μm stacks of 60 images at a 0.22 μm Z resolution were imaged for all conditions. The mean fluorescence of the different slices in the stacks was measured and a standard deviation was computed from the aggregated data per slice. The mean fluorescence with the corresponding standard deviations per slice was then plotted as a function of depth with the start of the stack set to zero.

Ex Vivo Biopsy Analysis

Polarized In Vitro Organ Culture (pIVOC): pIVOC experiments of colon biopsies were performed as described (Cell Host Microbe 12:47-59, 2012). Bacterial infections were conducted using microaerophilic preconditioned media or buffers. *L. monocytogenes* was added at a final $OD_{600}$=0.2 to the apical side of biopsies and $H_2O_2$ release was measured. Controls were either non-infected biopsies or biopsies pretreated with 20 μM DPI for 20 min before addition of *C. jejuni* or *L. monocytogenes* to the top chamber.

Ligated Rabbit Ileal Loops

Female rabbits (Chinchilla breed) were starved for 2 h prior to infection. Anesthesia was performed iv with ketamine (35 mg/kg) and xylazine (5 mg/kg). The incision line was injected subcutaneously with 2 ml xylazine 1%. After laparotomy four ileal loops (5 cm in length) were isolated and ligated. The loops were injected with either PBS, *C. jejuni* 81-176 or *L. monocytogenes* EDGe using 1 ml of culture at $OD_{600}$=0.3 in PBS (pH7.4). For each microorganism 3 rabbits were used. After closure of the abdomen rabbits were placed in cages for 180-360 minutes (*C. jejuni*) or 90-180 minutes (*L. monocytogenes*). Rabbits were sacrificed by intravenous injection of sodium pentobarbital (120 mg/kg). Fluid accumulated in each loop was collected separately and spun at 1000 rpm for 5 min to remove debris, followed by centrifugation at 5000 rpm to collect bacteria.

In-Vivo Murine Colitis Model (Administration of $H_2O_2$-Producing Bacteria)

Wildtype mice were treated with $1 \times 10^9$ bacteria by daily oral gavage 5 days before, during colitis (3% DSS in water) and until the end of the experiment (day 16). On day 7 of DSS treatment, DSS was replaced with water to enable the healing process. *Lactobacillus johnsonii* wildtype (NCC533, $H_2O_2$ production) enhances tissue restitution and reduces inflammation, while an isogenic *L. johnsonii* mutant (NCC9360, Δnfr, deletion of the $H_2O_2$-generating enzyme) is not effective. Daily administration of low nanomolar $H_2O_2$ accelerates recovery after insult (a—disease index, NCC533 triangle, c-body weight), downregulates inflammation (b, colon length as indicator of inflammation), and supports rapid tissue restitution (d-H&E staining of colon day 11). One-way Anova with Tukey post-hoc test; p=0.01, *p=0.001.

In-Vivo Murine Colitis Model (Administration of $H_2O_2$-Producing Capsules)

The source for nanomolar to low micromolar release of $H_2O_2$ in the intestine is controlled release capsules containing the enzyme glucose oxidase and its substrate glucose, albeit other combinations or sources can be used. Capsules containing a source for generating $H_2O_2$ in the intestine or control capsules (e.g. empty capsules, heat-inactivated enzyme, absence of substrate) are given once or multiple times daily by oral gavage at the onset of acute disease (day 0), at the height of disease (time varies dependent on the model) or when the healing process begins (time varies). Mice are monitored daily for weight and the extent of disease is scored according to an animal welfare and colitis adjusted scale. Animals are sacrificed at various time points to assess inflammation and tissue injury/tissue restitution. These parameters are determined by procedures including colon length measurement, immunohistochemistry with stains (e.g. H&E, Mason's), immunofluorescence using antibodies (e.g. anti-mucin 2) or staining with proliferation markers (e.g. BrdU). Markers of inflammation also include recruitment of immune cells, chemokine and cytokine levels in the mucosa and blood, measurement of mucus density, rheology and chemical composition, as well as microbiome and metabolome composition and quantitative parameters (e.g. cytokines, chemokines). Pharmacokinetic in vitro, ex vivo and in vivo studies are performed according to reported best practice, and safety and efficacy studies (up to 10 weeks) with and without prior insult to determine putative physiological changes due to prolonged $H_2O_2$ delivery and the ability to resist an acute colitis insult.

The invention claimed is:

1. A method for the treatment of inflammatory bowel disease in a mammal in need thereof, in which the method comprises a step of orally administering to the mammal a delivery system comprising hydrogen peroxide or a hydrogen peroxide generator system, wherein the delivery system is formulated for oral delivery and release of the hydrogen peroxide or hydrogen peroxide generator system in-situ at a target location in the mammalian gastrointestinal tract.

2. A method according to claim 1, in which the delivery system is formulated for release of the hydrogen peroxide or the hydrogen peroxide generator system in-situ in the colon.

3. A method according to claim 1, in which the hydrogen peroxide generator system comprises an enzyme and substrate configured to react in-situ at a target location in the mammalian gastrointestinal tract to produce hydrogen peroxide.

4. A method according to claim 1, in which the hydrogen peroxide generator system comprises an enzyme and substrate configured to react in-situ at a target location in the mammalian gastrointestinal tract to produce hydrogen peroxide, in which the substrate is glucose and the enzyme is glucose oxidase.

5. A method according to claim 1, in which the hydrogen peroxide generator system is substantially free of water.

6. A method according to claim 3, in which the hydrogen peroxide generator system is configured to keep the enzyme and substrate separate prior to release of the enzyme and substrate at the target location in the gastrointestinal tract.

7. A method according to claim 3 in which the enzyme is provided as a first particulate composition and the substrate is provided as a second particulate composition, optionally in which the first particulate composition and second particulate composition are each, independently, selected from microparticles, microspheres, nanoparticles, and granulated particles.

8. A method according to claim 7, in which the first and second particulate compositions are contained within a container configured to release the compositions at a target location within the gastrointestinal tract, in which the container is optionally an enteric coating.

9. A method according to claim 1, in which the delivery system comprises hydrogen peroxide.

10. A method according to claim 1, in which the delivery system comprises a polymeric matrix configured for slow release of hydrogen peroxide in-situ at the target location in the gastrointestinal tract.

11. A method according to claim 1, in which the hydrogen peroxide generator system comprises an active agent capable of localised stimulation of the mammalian epithelial tissue to produce hydrogen peroxide in-situ at the target location in the gastrointestinal tract, in which the active agent is optionally an agonist that enhances NOX1 or DUOX2 expression and/or activity.

12. A method according to claim 1, in which the hydrogen peroxide generator system is a bacterium that produces hydrogen peroxide.

13. A method according to claim 1, in which the hydrogen peroxide generator system is a bacterium that produces hydrogen peroxide, and in which the bacterium is genetically engineered to overexpress hydrogen peroxide.

14. A method according to claim 1, in which the delivery system is configured to release or generate 5 nmol to 20 µmol hydrogen peroxide in-situ at the target location in the gastrointestinal tract.

15. A method according to claim 1, in which the inflammatory bowel disease is ulcerative colitis or Crohn's disease, optionally in which the delivery system is administered during a remission phase of the disease to treat acute recurrence of the symptoms of the disease.

* * * * *